(12) United States Patent
Falk

(10) Patent No.: US 8,557,260 B2
(45) Date of Patent: Oct. 15, 2013

(54) COMPOSITION COMPRISING AT LEAST TWO DIFFERENT CYCLOALKYLMETHICONES AND USE THEREOF

(75) Inventor: Benjamin Falk, Yorktown Heights, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 413 days.

(21) Appl. No.: 12/640,235

(22) Filed: Dec. 17, 2009

(65) Prior Publication Data

US 2010/0158834 A1 Jun. 24, 2010

Related U.S. Application Data

(60) Provisional application No. 61/203,082, filed on Dec. 18, 2008.

(51) Int. Cl.
*A61K 9/00* (2006.01)

(52) U.S. Cl.
USPC .......................................................... 424/400

(58) Field of Classification Search
None
See application file for complete search history.

(56) References Cited

U.S. PATENT DOCUMENTS

| | | | |
|---|---|---|---|
| 2,495,363 A | 1/1950 | Barry et al. | |
| 4,526,780 A | 7/1985 | Marschner et al. | |
| 5,486,635 A * | 1/1996 | Okawa | 556/437 |
| 6,046,156 A | 4/2000 | Perry | |
| 6,054,547 A | 4/2000 | Perry et al. | |
| 6,060,546 A | 5/2000 | Powell et al. | |
| 6,075,111 A | 6/2000 | Perry et al. | |
| 6,077,923 A | 6/2000 | Perry et al. | |
| 6,083,901 A | 7/2000 | Perry et al. | |
| 6,153,578 A | 11/2000 | Perry | |
| 6,271,295 B1 | 8/2001 | Powell et al. | |
| 2010/0028391 A1 * | 2/2010 | Okawa et al. | 424/401 |

FOREIGN PATENT DOCUMENTS

GB 659011 10/1951

* cited by examiner

*Primary Examiner* — Anand Desai
*Assistant Examiner* — Melissa Mercier
(74) *Attorney, Agent, or Firm* — Dominick G. Vicari; Kenneth S. Wheelock

(57) ABSTRACT

A cosmetic composition includes comprising a blend of cycloalkylmethicones comprising at least two different cycloalkylmethicones having general formula I:

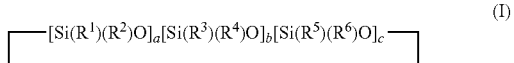

where $R^1$ is a hydrocarbon radical containing about 2 to about 4 carbon atoms; $R^2$, $R^3$, $R^4$, $R^5$, and $R^6$ are independently selected from the group consisting of a hydrocarbon radical containing about 1 to about 4 carbon atoms;
a is a positive number between $0<a<5$;
b and c are independently selected from 0 to 5 wherein $(a+b+c) \leq 5$; and
wherein the rates of evaporation of the composition as measured in accordance with standard DIN 53249 test is from about 80% to about 99% by weight loss in about 200 to about 6000 minutes, more preferably in about 200 to about 1000 minutes, and even more preferably in about 200 to about 500 minutes.

19 Claims, No Drawings

COMPOSITION COMPRISING AT LEAST TWO DIFFERENT CYCLOALKYLMETHICONES AND USE THEREOF

CROSS REFERENCE TO RELATED APPLICATIONS

The present application claims priority to U.S. Provisional Application No. 61/203,082 filed Dec. 18, 2008, which is herein incorporated by reference.

FIELD OF THE INVENTION

The present invention relates to compositions comprising a blend of at least two alkylmethylcyclic siloxanes.

BACKGROUND OF THE INVENTION

U.S. Pat. No. 2,495,363 describe the synthesis and composition of ethylmethylcylic siloxanes and linear polymers. This patent does not discuss a use of the cyclic silicones as volatile carriers and does not disclose volatility rates.

GB 659011 describes the process to manufacture cyclic and linear ethymethyl siloxanes.

U.S. Pat. No. 4,526,780 discloses the uses of a silicone with the composition of $[-R_2SiO-]_n$ wherein R is alkyl of 1 to 4 carbon atoms and n is 3 to 10, preferably from 3 to 7 in an antiperspirant composition. However, the volatility limitation is not disclosed nor does this patent disclose the use of mixtures of cyclic silicones to achieve the desired volatility. Therefore, what is needed in the industry is a composition comprising at least two different cycloalkylmethicones that can be used to produce cosmetic compositions having desired volatility profiles.

The present invention provides these types of compositions and cosmetics that have the desired volatility profile that is conducive for cosmetic compositions.

SUMMARY OF THE INVENTION

The present invention provides a cosmetic composition comprising a blend of cycloalkylmethicones comprising at least two different cycloalkylmethicones having general formula I:

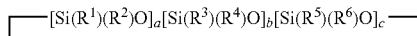

wherein $R^1$ is a hydrocarbon radical containing about 2 to about 4 carbon atoms;
$R^2$, $R^3$, $R^4$, $R^5$, and $R^6$ are independently selected from the group consisting of a hydrocarbon radical containing about 1 to about 4 carbon atoms;
a is a positive number between $0<a<5$;
b and c is independently selected from 0 to 5 wherein $(a+b+c)\leq 5$; and
wherein the rates of evaporation of the composition as measured in accordance with standard DIN 53249 test is from about 80% to about 95% by weight loss in about 200 to about 6000 minutes, more preferably in about 200 to about 1000 minutes, and even more preferably in about 200 to about 500 minutes.

Another embodiment of the present invention is directed to a novel blend of cycloalkylmethicones comprising at least two different cycloalkylmethicones having general formula I:

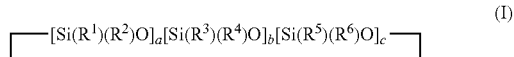

where $R^1$ is a hydrocarbon radical containing 2 to 4 carbon atoms;
$R^2$, $R^3$, $R^4$, $R^5$, and $R^6$ are independently selected from the group consisting of a hydrocarbon radical containing 1 to 4 carbon atoms;
a is a positive number between $0<a<5$;
b and c is independently selected from 0 to 5 wherein $(a+b+c)\leq 5$;
wherein the rates of evaporation of the composition as measured in accordance with standard DIN 53249 test is from about 90% to 99% by weight loss in about 250 to about 8000 minutes, more preferably in about 250 to about 2000 minutes and even more preferably in about 250 to about 550 minutes.

Yet another embodiment of the present invention is directed to a novel blend of cycloalkylmethicones comprising at least two different cycloalkylmethicones having general formula I:

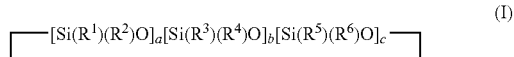

where $R^1$ is a hydrocarbon radical containing 2 to 4 carbon atoms;
$R^2$, $R^3$, $R^4$, $R^5$, and $R^6$ are independently selected from the group consisting of a hydrocarbon radical containing 1 to 4 carbon atoms;
a is a positive number between $0<a<5$;
b and c is independently selected from 0 to 5 wherein $(a+b+c)\leq 5$;
wherein the rates of evaporation of the composition as measured in accordance with standard DIN 53249 test is from about 95 to about 100% by weight loss after about 1000 minutes more preferably after about 750 minutes and even more preferably in about 500 minutes.

The present invention may be used as or at least in part of a cosmetic composition whereas the rate of evaporation is desired upon application of a formulation to a surface.

DETAILED DESCRIPTION OF THE INVENTION

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, a aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges. As used herein, integer values of stoichiometric subscripts refer to molecular species and non-integer values of stoichiometric subscripts refer to a mixture of molecular species on a molecular weight average basis, a number average basis or a mole fraction basis. In the case of mixtures of the compounds of the present invention, it should be readily apparent that the stoichiometric subscripts of mixtures would have average values for the subscripts that may be either integral or non-integral in contrast to those of pure compounds.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The compositions of the present invention may be utilized as pure components, mixtures, or emulsions. As is generally known, emulsions comprise at least two immiscible phases one of which is continuous and the other which is discontinuous. Further emulsions may be liquids or gases with varying viscosities or solids. Additionally the particle size of the emulsions may render them microemulsions and when sufficiently small microemulsions are used the emulsions may be transparent. Further, it is also possible to prepare emulsions of emulsions and these are generally known as multiple emulsions. These emulsions may be:

1) aqueous emulsions wherein the discontinuous phase comprises water and the continuous phase comprises the composition of the present invention;
2) aqueous emulsions wherein the discontinuous phase comprises the composition of the present invention and the continuous phase comprises water;
3) non-aqueous emulsions wherein the discontinuous phase comprises a non-aqueous hydroxylic solvent and the continuous phase comprises the composition of the present invention; and
4) non-aqueous emulsions wherein the continuous phase comprises a non-aqueous hydroxylic organic solvent and the discontinuous phase comprises the composition of the present invention.

Personal Care

In a preferred embodiment, the cyclic siloxane of the present invention comprises, per 100 parts by weight ("pbw") of the personal care composition, from 0.1 to 99 pbw, more preferably from 0.5 pbw to 60 pbw and still more preferably from 1 to 40 pbw.

The volatile cyclic siloxane compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and, when sufficiently small, microemulsions may be transparent. Further it is also possible to prepare emulsions of emulsions and these are generally known as multiple emulsions. These emulsions may be:

1) aqueous emulsions where the discontinuous phase comprises water and the continuous phase comprises the volatile cyclic silicone of the present invention;
2) aqueous emulsions where the discontinuous phase comprises the volatile cyclic silicone of the present invention and the continuous phase comprises water;
3) non-aqueous emulsions where the discontinuous phase comprises a non-aqueous hydroxylic solvent and the continuous phase comprises the volatile cyclic silicone of the present invention; and
4) non-aqueous emulsions where the continuous phase comprises a non-aqueous hydroxylic organic solvent and the discontinuous phase comprises the volatile cyclic silicone of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the volatile cyclic silicone of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the organo modified disiloxane surfactant. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the volatile cyclic silicone of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the volatile cyclic silicone, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the organo modified disiloxane surfactant, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

In another useful embodiment of this invention, a skin care or hair care composition, and another volatile component, such as, for example dodecamethylcyclohexasiloxane, decamethylcyclotetrasiloxane, octamethylcylcosiloxane, isododecane, 3ethyl-1,1,1,3,5,5,5-heptamethyltrisiloxane, isohexadecane, capryl methicone, ethyl alcohol, hexamethyldisiloxane, isobutene, and linear low molecular weight silicones.

The uses of the compositions of the present invention are not restricted to personal care compositions, other products such as waxes, polishes and textiles treated with the compositions of the present invention are also contemplated.

Compositions of this invention can be produced by conventional processes for making suspension or emulsion solids or soft-solids. Such processes involve forming a heated mixture of the composition at a temperature which is sufficiently elevated that all the esterified saccharide structurant dissolves, pouring that mixture into a mold, which may take the form of a dispensing container, and then cooling the mixture whereupon the structurant solidifies into a network of interconnected fibers extending through the water-immiscible liquid phase.

In a suitable procedure for making emulsion formulations, a solution of the esterified structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied in aqueous solution which can be utilized as is). This solution of antiperspirant active, which will become the disperse phase is preferably heated to a temperature similar to that of the continuous phase with structurant therein, but without exceeding the boiling point of the solution, and then mixed with the continuous phase. Alternatively, the solution is introduced at a rate, which maintains the temperature of the mixture. If necessary a pressurized apparatus could be used to allow a higher temperature to be reached, but with the structurant materials of this invention this is usually unnecessary. After the two phases are mixed, the resulting mixture is filled into dispensing containers, typically at a temperature 5 to 30 degrees C. above the setting temperature of the composition, and allowed to cool.

Cooling may be brought about by nothing more than allowing the container and contents to cool. Cooling may be assisted by blowing ambient or even refrigerated air over the containers and their contents.

SYNTHETIC EXAMPLES

Methylpropylcyclictrimer and Methylpropylcyclictetramer Production

Procedure:

Distilled water (2000 mL) was added to a 5000 mL 4 neck round bottom flask having a drain and a water-cooling jacket. The flask was equipped with an overhead stirrer rotating at 380 rpm, a Friedrichs condenser, and an addition funnel. A nitrogen blank was used along with a thermocouple to monitor temperature. Methylpropyldichlorosilane (1840 mL) was added drop-wise over 4 hr using the addition funnel while maintaining a temperature below 30° C. The reaction was allowed to stir overnight. The stirrer was stopped and the product was allowed to separated into 2 distinct layers. The aqueous bottom layer was drained off. Then distilled water (1000 mL) was added as a wash and mixed at 380 rpm for 10 min. The liquid layers were allowed to separate for 25 min. A second aliquot of distilled water (1000 mL) was added as a wash to the flask and stirred at 430 rpm for 10 min. the bottom water layer was drained off 30 min later. A KOH solution (1000 mL of 0.1N) was added and stirred for 30 min at 410 rpm to neutralize the reaction. Mixing was stopped. Sodium chloride (160 g) and anhydrous ether (150 mL) was added to aid in separation. The aqueous layer was removed. Stearyl alcohol (36.15 g) and 45 percent KOH solution (110 g) was added to the vessel. A short head condenser was added to the flask and a heating mantle. The water was removed by heating the reactor to 150° C. The short path distillation head was replace with an 18-inch Vigereaux column and a vacuum distillation head. Cuts were taken at temperatures ranging from 107.1° C. up to 125.6° C. and vacuum was between 12 and 13 Torr.

The total distillate yield was 971.9 g and was composed of 1,3,5-tripropyl-1,3,5-trimethylcyclotrisiloxane and 1,3,5,7-tetrapropyl-1,3,5,7-tetramethylcyclotetrasiloxane with trace amounts of higher molecular weight cyclics. The distillates were combined in a 2 L round bottom flask and distilled through a 3 foot long perforated plate column. The 1,3,5-tripropyl-1,3,5-trimethylcyclotrisiloxane (373.6 g) distilled at 100.2C to 101.5C and 12-10 Torr and the 1,3,5,7-tetrapropyl-1,3,5,7-tetramethylcyclotetrasiloxane (279.7 g) distilled at 137.2C to 134.8 C and 10 Torr.

Ethylmethylcyclictrimer and Ethylmethylcyclictetramer Production

Procedure:

Distilled water (2000 mL) was added to a 5000 mL 4 neck round bottom flask having a drain and a water-cooling jacket. The flask was equipped with an overhead stirrer rotating at 380 rpm, a Friedrichs condenser, and an addition funnel. A nitrogen blank was used along with a thermocouple to monitor temperature. Ethylmethyldichlorosilane (2 kg) was added drop-wise over 4 hr using the addition funnel while maintaining a temperature below 30° C. The reaction was allowed to stir overnight. The stirrer was stopped and the product was allowed to separated into 2 distinct layers. The aqueous bottom layer was drained off. Then distilled water (1000 mL) was added as a wash and mixed at 380 rpm for 10 min. The liquid layers were allowed to separate for 25 min. A second aliquot of distilled water (1000 mL) was added as a wash to the flask and stirred at 430 rpm for 10 min. the bottom water layer was drained off 30 min later. A sodium bicarbonate solution (1000 mL of 7.8 wt %) was added and stirred for 30 min at 410 rpm to neutralize the reaction.

Mixing was stopped. The aqueous layer was removed, Stearyl alcohol (36.15 g) and 45 percent KOH solution (110 g) was added to the vessel. A short head condenser was added to the flask and a heating mantle. The water was removed by heating the reactor to 150° C. The short path distillation head was replace with an 18-inch Vigereaux column and a vacuum distillation head. Cuts were taken at temperatures ranging from 107.1° C. up to 125.6° C. and vacuum was between 12 and 13 Torr. The total distillate yield was 971.9 g and was composed of 1,3,5-triethyl-1,3,5-trimethylcyclotrisiloxane and 1,3,5,7-tetraethyl-1,3,5,7-tetramethylcyclotetrasiloxane with trace amounts of higher molecular weight cyclics. The distillates were combined in a 2 L round bottom flask and distilled through a 3 foot long perforated plate column. The 1,3,5-triethyl-1,3,5-trimethylcyclotrisiloxane (514.3 g) distilled at 67-71° C. and 9-10 Torr and the 1,3,5,7-tetraethyl-1,3,5,7-tetramethylcyclotetrasiloxane (364.7 g) distilled at 102° C. and 10 Torr,

APPLICATION EXAMPLES

Example A=1,3,5-triethyl-1,3,5-trimethylcyclotrisiloxane

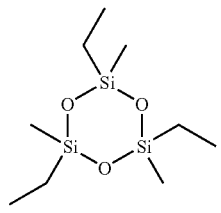

Example B=1,3,5,7-tetraethyl-1,3,5,7-tetramethylcyclotetrasiloxane

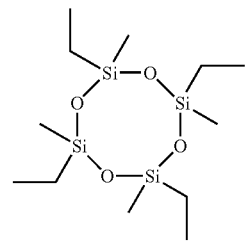 [SMILES: CC[Si]1(C)O[Si](C)(CC)O[Si](C)(CC)O[Si](C)(CC)O1]

Example
C=1,3,5,trimethyl-1,3,5-tripropylcyclotrisiloxane

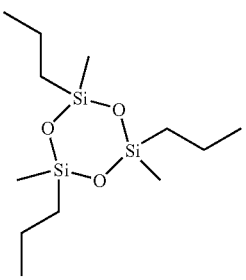 [SMILES: CCC[Si]1(C)O[Si](C)(CCC)O[Si](C)(CCC)O1]

Example D=1,3,5,7-tetramethyl-1,3,5,7-tetrapropyl-cyclotetrasiloxane

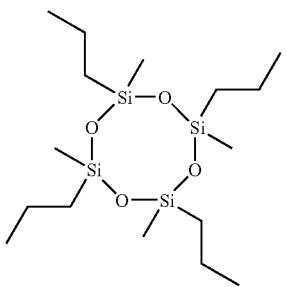 [SMILES: CCC[Si]1(C)O[Si](C)(CCC)O[Si](C)(CCC)O[Si](C)(CCC)O1]

Compositions

|  | Example A | Example B | Example C | Example D |
|---|---|---|---|---|
| Blend 1 | 45.0% | 55.0% |  |  |
| Blend 2 |  |  | 75.0% | 25.0% |
| Blend 3 | 91.1% | 8.9% |  |  |
| Blend 4 |  |  | 80.0% | 20.0% |

The volatility of this invention were determined in accordance with DIN 53249 by
1. weighing a round filter paper of diameter 150 mm;
2. applying a 0.3 g sample using a pipette, and immediately weight the filter and
3. weighing the filter at 5 min intervals at Room Temperature (25° C.) in a draft-free place.
4. In each case amounts were weighed to an accuracy of about 0.001 g.

Volatility Data

|  | Time (sec) Volatility (% Evaporated) | | |
|---|---|---|---|
|  | 80% | 90% | 95% |
| Blend 1 | 925 | 1275 | 1600 |
| Blend 2 | 5770 | 7000 | 8500 |
| Blend 3 | 250 | 280 | 375 |
| Blend 4 | 300 | 400 | 550 |

APPLICATION EXAMPLES

Below is a list of example cosmetic formulations using the cyclic silicones of the present invention. Two separate blends of ethyl methyl cyclic silicones and propylmethylcyclic silicones were made. The results are shown in each application example. The stability was determined by placing 50 g of each formulation in a 25° C. and a 50° C. oven. If the formulation separated after two weeks the formulation failed stability. The viscosities were taken the day the formulations were made using a Brookfield viscometer.

Example 1

Antiperspirant Solid

| | Formulation | | | | |
|---|---|---|---|---|---|
| Ingredient | F1 | F2 | F3 | F4 | Function |
| Decamethylcyclopentasiloxane | 51 | | | | Actives carrier |
| Hexamethyldisiloxane | | 51 | | | Actives carrier |
| Blend 1 | | | 51 | | Actives carrier |
| Blend 2 | | | | 51 | Actives carrier |
| Dimethicone (SF96-100) (1) | 5 | 5 | 5 | 5 | Emollient/Anti-whitening |
| Stearyl Alcohol | 19 | 19 | 19 | 19 | Structuring agent |
| Hydrogenated Castor Oil (mp 70° C.) | 3 | 3 | 3 | 3 | Structuring agent/Emollient |
| Talc | 4 | 4 | 4 | 4 | Smooth feel |
| Glyceryl Stearate (and) PEG-100 Stearate (2) | 2 | 2 | 2 | 2 | Emulsifier |
| Aluminum Zirconium Tetrachlorohydrex Gly | 16 | 16 | 16 | 16 | Antiperspirant active |

Procedure:
1. Actives carrier, dimethicone and stearyl alcohol were mixed together.
2. To the above mixture was added antiperspirant active, talc and glyceryl stearate (and) PEG-100 stearate.
3. This was then heated to 75° C. and stirred with moderate agitation until all wax had melted.
4. The hydrogenated castor oil was pre-melted and added to mixture as a liquid and stirred for 15 minutes.
5. This mixture was then cooled to 55° C. with continued mixing and poured into container.

Trade Names/Suppliers: (1) Momentive Performance Materials (2) Uniqema, Inc.

| Stability Test | Room Temp 2 weeks | 50° C. Oven 2 weeks |
|---|---|---|
| F1 | Passed | Passed |
| F2 | Passed | Passed |
| F3 | Passed | Passed |
| F4 | Passed | Passed |

Example 2

Skin Lotion

| | Formulation | | | | |
|---|---|---|---|---|---|
| | Part/Wt (%) | | | | |
| Ingredient | F5 | F6 | F7 | F8 | Function |
| PART A | | | | | |
| Cyctopentasiloxane (and) 20/15Dimethicone (SFI540) | 2.5 | 2.5 | 2.5 | 2.5 | Emulsifier |
| Decamethylcyclopentasiloxane | 16 | | | | Emollient |
| Hexamethyldisiloxane | | 16 | | | Emollient |
| Blend 1 | | | 16 | | Emollient |
| Blend 2 | | | | 16 | Emollient |
| Cyclopentasiloxane (and) Dimethicone (SFI214) (1) | 7.5 | 7.5 | 7.5 | 7.5 | Emollient |
| PART B | | | | | |
| Glycerin | | | 3 | | Humectant |
| Sodium Chloride | | | 1 | | Stabilizer |
| Polysorbate-80 | | | 0.2 | | Emulsifier |
| Quaternium-15 | | | 0.1 | | Preservative |
| Deionized Water | | | 69.7 | | Diluent |

Procedure:

1. The Part A ingredients were combined together in order shown, thoroughly mixing each component until homogeneous before adding the next ingredient.
2. All Part B ingredients were mixed together.
3. Slowly, the Part B mixture was added to Part A with good mixing. The agitation was gradually increased high shear as mixture thickened. The agitation was continues for a further 10 minutes, when the mixture became very thick.
4. This was then submitted to a blender for 2 minutes.

Trade Names/Suppliers: (1) Momentive Performance Materials

| Stability Test | Room Temp 2 weeks | 50° C. Oven 2 weeks |
|---|---|---|
| F5 | Passed | Passed |
| F6 | Passed | Passed |
| F7 | Passed | Passed |
| F8 | Passed | Passed |

| | Viscosity (CP) |
|---|---|
| F5 | 41160 |
| F6 | 32520 |
| F7 | 35160 |
| F8 | 30960 |

Example 3

Light Satin Lotion

| | Part/Wt (%) | | | | |
|---|---|---|---|---|---|
| | F9 | F10 | F11 | F12 | Function |
| PART A | | | | | |
| Sorbitan Oleate | 0.60 | 0.60 | 0.60 | 0.60 | Co-emulsifier |
| Cyclopentasiloxane (and) PEG/PPG-20/15 Dimethicone (SF1540) (1) | 2.50 | 2.50 | 2.50 | 2.50 | Emulsifier |
| Cyclopentasiloxane (and) C30-45 Alkyl Cetearyl Dimethicone Crosspolymer (Velvesil@125) (1) | 7.50 | 7.50 | 7.50 | 7.50 | Sensory Enhancer |
| Decamethylcyclopentasiloxane | 16.50 | | | | Emollient |
| Hexamethyldisiloxane | | 16.50 | | | Emollient |
| Blend 1 | | | 16.50 | | Emollient |
| Blend 2 | | | | 16.50 | Emollient |
| PART B | | | | | |
| Butylene Glycol | | | 1.00 | | Humectant |
| Sodium Chloride | | | 1.00 | | Stabilizer |
| Quaternium-15 | | | 0.10 | | Preservative |
| Water | | | 70.80 | | Diluent |

Procedure:

1. Part A ingredients were combined in the order shown, thoroughly mixing each component until homogeneous before adding next ingredient.
2. All ingredients of Part B were mixed together and stirred well until homogeneous.
3. Slowly, the Part B mixture was added to Part A with good mixing. Gradually, the agitation was increased to high shear as the mixture thickened. The agitation was continued for 20 minutes.
4. This was then submitted to a blender for 2 minutes.

| Stability Test | Room Temp 2 weeks | 50° C. Oven 2 weeks |
|---|---|---|
| F9 | Passed | Passed |
| F10 | Passed | Passed |
| F11 | Passed | Passed |
| F12 | Passed | Passed |

| | Viscosity (CP) |
|---|---|
| F9 | 50280 |
| F10 | 28080 |
| F11 | 45000 |
| F12 | 39700 |

Example 4

Sheer Silky Make-Up Foundation

|  | F13 | F14 | F15 | F16 | Function |
|---|---|---|---|---|---|
|  | Part/Wt (%) | | | | |
| PART A | | | | | |
| Cyclopentasiloxane (and) PEG/PPG-20-15 Dimethicone (SFI540) (1) | 5.12 | 5.12 | 5.12 | 5.12 | Emulsifier |
| Cyclopentasiloxane (and) Dimethicone/Vinyl Dimethicone Crosspolymer (SFE839) (1) | 3 | 3 | 3 | 3 | Sensory Enhancer |
| C30-45 Alkyl Dimethicone (SFI642) (1) | 2 | 2 | 2 | 2 | Thickener/ Emollient |
| Decamethylcyclopentasiloxane | 24 | | | | |
| Hexamethyldisiloxane | | 24 | | | |
| Blend 1 | | | 24 | | |
| Blend 2 | | | | 24 | Emollient |
| Phenyl Trimethicone (SFI550) (1) | 3 | 3 | 3 | 3 | Emollient/ Shine Enhancer |
| Titanium Dioxide (2) | 7.6 | 7.6 | 7.6 | 7.6 | Pigment |
| Yellow Iron Oxides (3) | 2.8 | 2.8 | 2.8 | 2.8 | Pigment |
| Red Iron Oxides (3) | 1.3 | 1.3 | 1.3 | 1.3 | Pigment |
| Black Iron Oxides (3) | 0.18 | 0.18 | 0.18 | 0.18 | Pigment |
| Sorbitan Oleate | 0.5 | 0.5 | 0.5 | 0.5 | Co-Emulsifier |
| PART B | | | | | |
| Deionized Water | 49.3 | 49.3 | 49.3 | 49.3 | Diluent |
| Polysorbate-20 | 0.2 | 0.2 | 0.2 | 0.2 | Emulsifier |
| Sodium Chloride | 1 | 1 | 1 | 1 | Stabilizer |

Procedure:

1. The ingredients of Part A were combined, in order shown, thoroughly mixing each component until homogenous before adding the next ingredient. This was then heated to 60° C. and mixed until SF1642 was dissolved.
2. In a separate vessel, the ingredients of Part B were combined in the order shown.
3. Slowly Part B was added to Part A with good mixing.
4. The mixture was poured into suitable containers.

Trade Names/Suppliers: (1) Momentive Performance Materials (2) IN 80° C., Kobo Products (3) Kobo Products

| Stability Test | Room Temp 2 weeks | 50° C. Oven 2 weeks |
|---|---|---|
| F13 | Failed | Failed |
| F14 | Failed | Failed |
| F15 | Failed | Failed |
| F16 | Failed | Failed |

| | Viscosity (cP) |
|---|---|
| F13 | 2904 |
| F14 | 1500 |
| F15 | 1812 |
| F16 | 1518 |

Example 5

Protective Facial Sunscreen with Superior Substantively

|  | F17 | F18 | F19 | F20 | Function |
|---|---|---|---|---|---|
|  | Part/Wt (%) | | | | |
| PART A | | | | | |
| Stearic Acid | 2.5 | 2.5 | 2.5 | 2.5 | Emulsifier |
| Cetyl Alcohol | 1.8 | 1.8 | 1.8 | 1.8 | Co-Emulsifier |
| DEA Cetyl Phosphate (1) | 2.5 | 2.5 | 2.5 | 2.5 | Co-Emulsifier |
| Diisostearoyl Trimethylolpropane Siloxy Silicate (SF1318) (2) | 5 | 5 | 5 | 5 | Emollient/ Film-former |
| Octyl Methoxycinnamate | 7 | 7 | 7 | 7 | UV absorber |
| Decamethylcyclopentasiloxane | 5 | | | | Emollient |
| Hexamethyldisiloxane | | 5 | | | Emollient |
| Blend 1 | | | 5 | | Emollient |
| Blend 2 | | | | 5 | Emollient |
| PART B | | | | | |
| Glycerin | 4 | 4 | 4 | 4 | Humectant |
| Quaternium-15 | 0.1 | 0.1 | 0.1 | 0.1 | Preservative |
| Xanthan Gum | 0.25 | 0.25 | 0.25 | 0.25 | Thickener/ Stabilizer |
| Water | 71.85 | 71.85 | 71.85 | 71.85 | Diluent |

Procedure:

1. Part A and B were mixed in separate containers to 85-90° C. with agitation.
2. Part A contents were added to Part B with high shear agitation.
3. Cool to room temperature with continued mixing.

Trade Names/Suppliers: (1) AmphisoFM, Givaudan, (2) Momentive Performance Materials

| Stability Test | Room Temp 2 weeks | 50° C. Oven 2 weeks |
|---|---|---|
| F17 | Passed | Passed |
| F18 | Passed | Failed |
| F19 | Passed | Passed |
| F20 | Passed | Passed |

| | Viscosity (cP) |
|---|---|
| F17 | 24360 |
| F18 | 8520 |
| F19 | 23280 |
| F20 | 27120 |

Example 6

Hair Cuticle Coat

| | Part/Wt (%) | | | | |
|---|---|---|---|---|---|
| Ingredient | F21 | F22 | F23 | F24 | Function |
| PART A | | | | | |
| Decamethylcyclopentasiloxane | 55.03 | | | | Carrier |

-continued

| Ingredient | F21 | F22 | F23 | F24 | Function |
|---|---|---|---|---|---|
| | Part/Wt (%) | | | | |
| Hexamethyldisiloxane | | 55.03 | | | Carrier |
| Blend 1 | | | 55.03 | | Carrier |
| Blend 2 | | | | 55.03 | Carrier |
| Dimethicone (1) | 9.97 | 9.97 | 9.97 | 9.97 | Conditioner |
| PART B | | | | | |
| Isohexadecane | 33 | 33 | 33 | 33 | Carrier |
| Octyl Methoxycinnamate | 2 | 2 | 2 | 2 | UV Absorber |

Procedure
1. Dimethicone was dissolved in di-t-butoxytetramethyldisiloxane with stirring at 75° C. for 6 hours.
2. All ingredients of Part B were mixed together and stirred well until homogeneous.
3. Slowly, the Part B mixture was added to Part A with good mixing. The agitation was continued for 30 minutes.

Trade Names/Suppliers: (1) Momentive Performance Materials

| Stability Test | Room Temp 2 weeks | 50° C. Oven 2 weeks |
|---|---|---|
| F21 | Passed | Passed |
| F22 | Passed | Passed |
| F23 | Passed | Passed |
| F24 | Passed | Passed |

| | Viscosity (cP) |
|---|---|
| F21 | 906 |
| F22 | 255 |
| F23 | 765 |
| F24 | 705 |

Example 7

Silicone Gel

An example of silicone gels were synthesized in various personal care solvents. The results are shown below. It is noted that the viscosity of the gels made with the ethylmethylcyclic silicone blend are most similar to the viscosity of the gels made with D5 (D5 is known to be decamethylcyclopentasiloxane).

Step One: Elastomer Powder.
A silicone hydride fluid (91.94 g) with the structure of $(CH_3)_3SiO[Si(CH_3)_2O]_{96}[Si(CH_3)(H)O]_4Si(CH_3)_3$, a silicone resin (10.96 g) with the structure $[(CH_2CH)Si(CH_3)_2O]_{0.34}[(CH_3)_3 SiO]_{0.01}[SiO_4]_{0.65}$, 1-Octadecene (5.62 g), and solvent (153.48 g) were charged into a ½ liter round bottom reaction kettle. The kettle was outfitted with a Teflon edged anchor stirrer, a thermocouple, and with a temperature controlled hot oil bath. The hot oil bath was set for 90° C. and the mixture was stirred at 50 RPM with a nitrogen purge. When the temperature of the reactants reached 80° C. Karstadt's reagent 0.25 ml (10 ppm Pt) was added. The material in the reactor gelled and turned to a powder in 1.5 hrs. The stirring was continued for an additional 30 min. The elastomer to solvent ratio was 40:60

Step Two: The Elastomer Powder Homogenization
The Elastomer Powder (37.59 g) was placed in a 250 ml wide mouth and additional solvent was added to bring the total weight to 100 g. The suspension was rapidly stirred with a Cowles blade. The mixture was left to stand for an hour then process through a Microfluidics model 110S homogenizer. Upon homogenization the material appeared to be a clear viscous gel. The viscosity was measured with a Brookfield DVII+Pro viscometer immediately following homogenization and again 3 days later.

| | Viscosity (cP) | |
|---|---|---|
| Solvent | Day 0 | Day 3 |
| Decamethylcyclotetrasiloxane Gel | 168000 | 180000 |
| Silsoft ETS Gel | 91000 | 155000 |
| Ethylmethylcyclic trimer/tetramer 50/50 Blend Gel | 149000 | 200000 |
| SF96-5 Gel | 41000 | 16000 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:
1. A composition comprising a blend of cycloalkylmethicones comprising at least two different cycloalkylmethicones having general formula I:

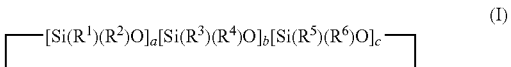

(I)

where $R^1$ is a hydrocarbon radical containing about 2 to about 4 carbon atoms;
$R^2$, $R^3$, $R^4$, $R^5$, and $R^6$ are independently selected from the group consisting of a hydrocarbon radical containing about 1 to about 4 carbon atoms;
a is a positive number between $0<a<5$;
b and c are independently selected from 0 to 5 wherein $(a+b+c) \leq 5$; and
wherein the rates of evaporation of the composition as measured in accordance with standard DIN 53249 test is from about 80% to about 99% by weight loss in about 200 to about 6000 minutes, wherein the composition is a cosmetic composition and wherein the blend of cycloalkylmethicones comprises from 0.1 to 99.0 percent by weight of the composition.

2. The composition of claim 1 wherein the cycloalkylmethicones are selected from the group consisting of 1,3,5-triethyl-1,3,5- trimethylcyclotrisiloxane, 1,3,5,7- tetraethyl-1,3,5,7-tetramethylcyclotetrasiloxane, 1,3,5,trimethyl-1,3,5-tripropylcyclotrisiloxane and 1,3,5 ,7-tetramethyl-1,3,5,7-tetrapropylcyclotetrasiloxane.

3. The composition of claim 1 comprising a blend of 1,3, 5-triethyl-1,3,5-trimethylcyclotrisiloxane, 1,3,5,7-tetraethyl-1,3,5,7-tetramethylcyclotetrasiloxane.

4. The composition of claim 1 comprising a blend of from 45 weight percent to 91.1 weight percent of 1,3,5-triethyl-1, 3,5-trimethylcyclotrisiloxane and from 8.9 weight percent to 55 weight percent of 1,3,5,7-tetraethyl-1,3,5,7-tetramethyl-cyclotetrasiloxane.

5. The composition of claim 1 comprising a blend of 1,3,5,trimethyl-1,3,5-tripropylcyclotrisiloxane and 1,3,5,7-tetramethyl-1,3,5,7-tetrapropylcyclotetrasiloxane.

6. The composition of claim 1 comprising a blend of 75 weight percent to 80 weight percent of 1,3,5,trimethyl-1,3,5-tripropylcyclotrisiloxane and 20 weight percent to 25 weight percent of 1,3,5,7-tetramethyl-1,3,5,7-tetrapropylcyclotetrasiloxane.

7. The composition of claim 1 wherein the blend of cycloalkylmethicones comprises from 0.5 to 60.0 percent by weight of the composition.

8. The composition of claim 1 wherein the blend of cycloalkylmethicones comprises from 1.0 to 40.0 percent by weight of the composition.

9. The composition of claim 1 wherein said composition is an aqueous emulsion where the discontinuous phase comprises water and the continuous phase comprises the blend of cycloalkylmethicones.

10. The composition of claim 1 wherein said composition is an aqueous emulsion where the discontinuous phase comprises the blend of cycloalkylmethicones and the continuous phase comprises water.

11. The composition of claim 1 comprising a non-aqueous organic hydroxylic solvent selected from the group consisting of alcohols, glycols, polyhydric alcohols, polymeric glycols and mixtures thereof, said non-aqueous organic hydroxylic solvents being liquid at ambient conditions.

12. The composition of claim 11 wherein said composition is a non-aqueous emulsion where the discontinuous phase comprises the non-aqueous hydroxylic organic solvent and the continuous phase comprises the blend of cycloalkylmethicones.

13. The composition of claim 11 wherein said composition is a non-aqueous emulsion where the discontinuous phase comprises the blend of cycloalkylmethicones and the continuous phase comprises the non-aqueous hydroxylic organic solvent.

14. The composition of claim 1 comprised in deodorants, antiperspirants, antiperspirant/deodorants, shaving products, skin lotions, moisturizers, toners, bath products, cleansing products, shampoos, conditioners, mousses, styling gels, hair sprays, hair dyes, hair color products, hair bleaches, waving products, hair straighteners, nail polish, nail polish remover, nails creams and lotions, cuticle softeners, sunscreen, insect repellent and anti-aging products, lipsticks, foundations, face powders, eye liners, eye shadows, blushes, makeup, mascaras or drug delivery systems for topical application of medicinal compositions that are to be applied to the skin.

15. The composition of claim 1 further comprising one or more of emollients, moisturizers, humectants, pigments, bismuth oxychloride, titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents, talc, kaolin, starch, modified starch, nylon, bentonite and organo-modified clays.

16. The composition of claim 1 further comprising an antiperspirant agent selected from the group consisting of aluminum halides, aluminum hydroxyhalides, and complexes or mixtures thereof with zirconyl oxyhalides and zirconyl hydroxyhalides.

17. The composition of claim 1 further comprising one or more skin care component selected from the group consisting of triglyceride esters, wax esters, alkyl or alkenyl esters of fatty acids or polyhydric alcohol esters, pigments, Vitamin A, Vitamin C, Vitamin E, titanium dioxide, zinc oxide, oxybenzone, octylmethoxy cinnamate, butylmethoxy dibenzoylmethane, p-aminobenzoic acid and octyl dimethyl-p-aminobenzoic acid.

18. The composition of claim 1 further comprising a volatile component selected from the group consisting of dodecamethylcyclohexasiloxane decamethylcyclotetrasiloxane, octamethylcylcosiloxane, isododecane, 3-ethyl-1,1,1,3,5,5,5-heptamethyltrisiloxane, isohexadecane, capryl methicone, ethyl alcohol, hexamethyldisiloxane, isobutene, and linear low molecular weight silicones.

19. The composition of claim 1 wherein the rate of evaporation of the composition as measured in accordance with standard DIN 53249 test is from about 80% to about 99% by weight loss in about 200 to about 500 minutes.

* * * * *